US012672849B1

(12) United States Patent
Beers et al.

(10) Patent No.: US 12,672,849 B1
(45) Date of Patent: Jul. 7, 2026

(54) ARTICULATED ULTRASOUND IMAGING PROBE FOR AN IMAGE-GUIDED BURR HOLE NEUROSURGERY PROCEDURE

(71) Applicant: GE Precision Healthcare LLC, Waukesha, WI (US)

(72) Inventors: Christopher Beers, State College, PA (US); Melanie Ann Keim, Pennsylvania Furnace, PA (US); Fredrik Gran, Limhamn (SE)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

(21) Appl. No.: 19/010,410

(22) Filed: Jan. 6, 2025

(51) Int. Cl.
 *A61B 8/00* (2006.01)
 *A61B 8/12* (2006.01)
(52) U.S. Cl.
 CPC .............. *A61B 8/4477* (2013.01); *A61B 8/12* (2013.01); *A61B 8/4494* (2013.01); *A61B 8/5246* (2013.01)
(58) Field of Classification Search
 CPC ....... A61B 8/4477; A61B 8/4494; A61B 8/12; A61B 8/5246
 See application file for complete search history.

(56) References Cited

U.S. PATENT DOCUMENTS

| | | | |
|---|---|---|---|
| 5,680,863 A | 10/1997 | Hossack et al. | |
| 7,399,284 B2 | 7/2008 | Miwa et al. | |
| 7,878,977 B2 | 2/2011 | Mo et al. | |
| 8,912,709 B2 | 12/2014 | Pollock et al. | |
| 11,738,214 B2 | 8/2023 | Carpentier et al. | |
| 2005/0215895 A1 | 9/2005 | Popp et al. | |
| 2007/0078345 A1* | 4/2007 | Mo .......................... | A61B 8/12 |
| | | | 600/459 |

(Continued)

FOREIGN PATENT DOCUMENTS

| | | |
|---|---|---|
| CN | 101152646 A | 4/2008 |
| WO | 99/48621 | 9/1999 |

OTHER PUBLICATIONS

Asencio-Cortes et al, Safety and Performance of a New Burr Hole Covering Device: Results of the Multicenter Cover Registry, Neurol Sug A Cent Eur Neurosurg, 2023, pp. 445-454, vol. 84.

(Continued)

*Primary Examiner* — Chao Sheng
(74) *Attorney, Agent, or Firm* — Daugherty & Del Zoppo, Co. LPA

(57) ABSTRACT

A side-fire ultrasound imaging probe is configured for an image-guided neurosurgery procedure through a burr hole in a skull of a patient. The side-fire ultrasound imaging probe includes an elongated shaft with a first end region, a second opposing end region, a long axis, at least a first rigid transducer array and a second rigid transducer array arranged in the first end region along the long axis of the elongated shaft, and an articulating region between the at least the first rigid transducer array and the second rigid transducer array. The side-fire ultrasound imaging probe further includes a handle with a first end region, wherein the first end region of the handle is coupled to the second opposing end region of the elongated shaft. A largest cross-sectional dimension of the first end region is smaller than a diameter of the burr hole in the skull of the patient.

16 Claims, 6 Drawing Sheets

(56) References Cited

U.S. PATENT DOCUMENTS

2018/0116519 A1*  5/2018  Piron ................... A61B 5/0059
2022/0087638 A1    3/2022  Hansen et al.

OTHER PUBLICATIONS

Ghoshal et al., A minimally invasive catheter-based ultrasound technology for therapeutic interventions in brain: initial preclinical studies, Neurosurg Focus, Feb. 2018, sheet 14, vol. 44, No. 2.
Christopher J.L. Lane, The inspection of curved components using flexible ultrasonic arrays and shape sensing fibres, Case Studies in Nondestructive Testing and Evaluation, 2014, vol. 1, pp. 13-18.

* cited by examiner

SCANPLANES

START

ADVANCE A BIFURCATED END REGION OF AN
ULTRASOUND IMAGE PROBE INTO A BURR HOLE — 1402

STEER AND/OR ARTICULATE BRANCHES OF THE BIFURCATED
END REGION TO TISSUE OF INTEREST TO SCAN — 1404

RECEIVE ECHOES FROM THE TRANSDUCER ARRAYS — 1406

PROCESS THE ECHOES TO GENERATE A COMPOSITE IMAGE — 1408

DISPLAY THE IMAGE — 1410

END

ARTICULATED ULTRASOUND IMAGING PROBE FOR AN IMAGE-GUIDED BURR HOLE NEUROSURGERY PROCEDURE

FIELD

The following generally relates to ultrasound imaging and more particularly to an articulated ultrasound imaging probe for image-guided burr hole neurosurgery procedure.

BACKGROUND

Ultrasound imaging provides a real-time image with information about the interior of an object or a subject such as tissue, organs, etc. An ultrasound imaging system includes an ultrasound imaging probe with a transducer array that transmits an ultrasound pressure field into an examination field of view. As the ultrasound pressure field traverses structure (e.g., of a sub-portion of an object or subject) in the field of view, portions of the ultrasound pressure field are attenuated, scattered, and/or reflected off the structure, with some of the reflections (echoes) traversing back towards the transducer array.

The transducer array receives the echoes and produces analog radio frequency (RF) signals indicative of the echoes. The RF signals are processed, e.g., amplified, converted to digital signals, beamformed, etc., to produce scan lines of RF data. With delay-and-sum beamforming, the digital signals are time delayed, weighted, and then summed to produce the scan lines of RF data. The scan lines of RF data are further processed (e.g., band-pass filtering, envelope detection, logarithmic compression, etc.), scan converted, and displayed as a frame/two-dimensional (2-D) B-mode image.

Ultrasound imaging is used in a wide range of medical applications. An example of a medical application includes ultrasound image-guided procedures such as an image-guided burr hole neurosurgery procedure. In general, a burr hole neurosurgery procedure is a microsurgery procedure performed through a hole in the skull that a neurosurgeon drills with a special drill. For this, an incision is made through the scalp, the skin muscles are lifted and folded back, and a burr hole is drilled in the skull. Burr hole procedures have been used for shunt placement, a brain lesion biopsy, puncture of an intracerebral abscess, a treatment, etc.

An example diameter of a burr hole in the skull for a neurosurgery procedure is in a range of four to fourteen millimeters (4-14 mm, such as 8-12 mm, etc.). To utilize an ultrasound imaging probe for guidance, the tip of the ultrasound imaging probe needs to be smaller than the diameter of the burr hole and additionally leave enough space for advancement of a surgical instrument. A non-limiting example of such a probe includes the N11C5s Transducer (a product of BK Medical, Denmark), which has an end-fire transducer in a rectangular tip with dimensions of 10×8.6 mm. Another example includes the S31KP Burr-Hole Guidance Transducer (a product of Fujifilm, USA), which has an end-fire transducer in a circular tip with a diameter of 12 mm.

For the procedure, the tip at the end of the shaft of the ultrasound imaging probe is inserted straight into and advanced through the burr hole. The end-fire transducer at the tip captures an image straight down, in-plane, along a direction of the shaft and the burr hole. Imaging quality, e.g., resolution, penetration, etc., is proportional to the acoustic aperture, i.e., a size of the dimension of the transducer array in azimuth (e.g., 10 mm and 12 mm in the above-noted probes). However, since the tip of the ultrasound imaging probe is limited by the diameter of burr hole (e.g., 4-14 mm, as noted above), the achievable imaging quality is limited by the diameter of burr hole.

In view of at least the foregoing, there is an unresolved need for an improved ultrasound imaging probe for image-guided burr hole neurosurgery procedure.

SUMMARY

Aspects of the application address the above matters, and others. This summary introduces concepts that are described in more detail in the detailed description. It should not be used to identify essential features of the claimed subject matter, nor to limit the scope of the claimed subject matter.

In one aspect, a side-fire ultrasound imaging probe is configured for an image-guided neurosurgery procedure through a burr hole in a skull of a patient. The side-fire ultrasound imaging probe includes an elongated shaft with a first end region, a second opposing end region, a long axis, at least a first rigid transducer array and a second rigid transducer array arranged in the first end region along the long axis of the elongated shaft, and an articulating region between the at least the first rigid transducer array and the second rigid transducer array. The side-fire ultrasound imaging probe further includes a handle with a first end region, wherein the first end region of the handle is coupled to the second opposing end region of the elongated shaft. A largest cross-sectional dimension of the first end region is smaller than a diameter of the burr hole in the skull of the patient.

In another aspect, a method for an image-guided neurosurgery procedure through a burr hole in a skull of a patient includes receiving echoes by at least a first rigid transducer array and a second rigid transducer array of a side-fire ultrasound imaging probe. The side-fire ultrasound imaging probe includes an elongated shaft with a long axis, the at least the first rigid transducer array and the second rigid transducer array arranged along the long axis, and an articulating region between the at least the first rigid transducer array and the second rigid transducer array. A largest cross-sectional dimension of the first end region is smaller than a diameter of the burr hole in the skull of the patient. The method further includes processing the echoes received by the at least a first rigid transducer array and a second rigid transducer array to generate a composite image with an acoustic aperture that is larger than an acoustic aperture of images generated for individual arrays of the at least the first rigid transducer array and the second rigid transducer array. The method further includes displaying the composite image on a display monitor.

In another aspect, a computer readable medium encoded with computer executable instructions, which, when executed by a processor, cause the processor to receive echoes by at least a first rigid transducer array and a second rigid transducer array of a side-fire ultrasound imaging probe during an image-guided neurosurgery procedure through a burr hole in a skull of a patient. The side-fire ultrasound imaging probe includes an elongated shaft with a long axis, the at least the first rigid transducer array and the second rigid transducer array arranged along the long axis, and an articulating region between the at least the first rigid transducer array and the second rigid transducer array. A largest cross-sectional dimension of the first end region is smaller than a diameter of the burr hole in the skull of the patient. The computer executable instructions further cause the processor to process the echoes received by the at least a first rigid transducer array and a second rigid transducer array to generate a composite image with an acoustic aperture that is larger than an acoustic aperture of images generated for individual arrays of the at least the first rigid transducer array and the second rigid transducer array. The wth computer executable instructions further cause the processor to display the composite image on a display monitor.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

DETAILED DESCRIPTION

Embodiments of the present disclosure will now be described, by way of example, with reference to the figures, in which an ultrasound imaging system includes an ultrasound imaging probe configured for ultrasound image-guided neurosurgery procedures through a burr hole in the skull of a patient. The ultrasound imaging probe includes a flexible elongated shaft with at least two rigid transducer arrays disposed along a long axis of the flexible shaft, where the at least two rigid transducer arrays are separated by a flexible gap of the flexible shaft, and the elongated flexible shaft is configured to articulate at the flexible gap only in-plane (i.e., in a direction of the imaging plane). In one instance, the at least two rigid transducer arrays are next to each other in a tip of the probe on the long axis. In one instance, the at least two rigid transducer arrays are parallel to each other is separate branches of the tip along the long axis.

As discussed above, a burr hole for ultrasound image-guided skull-based neurosurgery procedures has been around 4-14 mm in diameter, which limits a size of the tip of the probe to less than 4-14 mm in any direction, i.e., so that the tip of the ultrasound imaging probe and a surgical instrument such as a biopsy needle, etc. can simultaneously fit in the burr hole, which limits the size of the transducer array in azimuth and hence the acoustic aperture of the transducer array, which limits the achievable image quality. As described in greater detail below, the ultrasound imaging probe herein allows for an acoustic aperture that is not limited by the size of the burr hole or any single transducer array.

In one instance, the ultrasound imaging system is further configured to determine a relative position and orientation of each of the at least two transducer arrays with respect to each other based on images generated from the echoes received by the at least two transducer arrays, e.g., based on overlapping regions of the generated images. As such, the probe does not require position and orientation sensors in and/or on the shaft and/or transducer arrays to determine position and orientation information. In one instance, this allows for a smaller footprint of the tip and/or shaft relative to a configuration that includes position and orientation sensors in and/or on the shaft and/or transducer arrays. In addition, in one instance the position and orientation information are used to combine images from the different arrays to provide an increased acoustic aperture relative to the acoustic aperture of the individual arrays and hence improve image quality.

Figure 1:
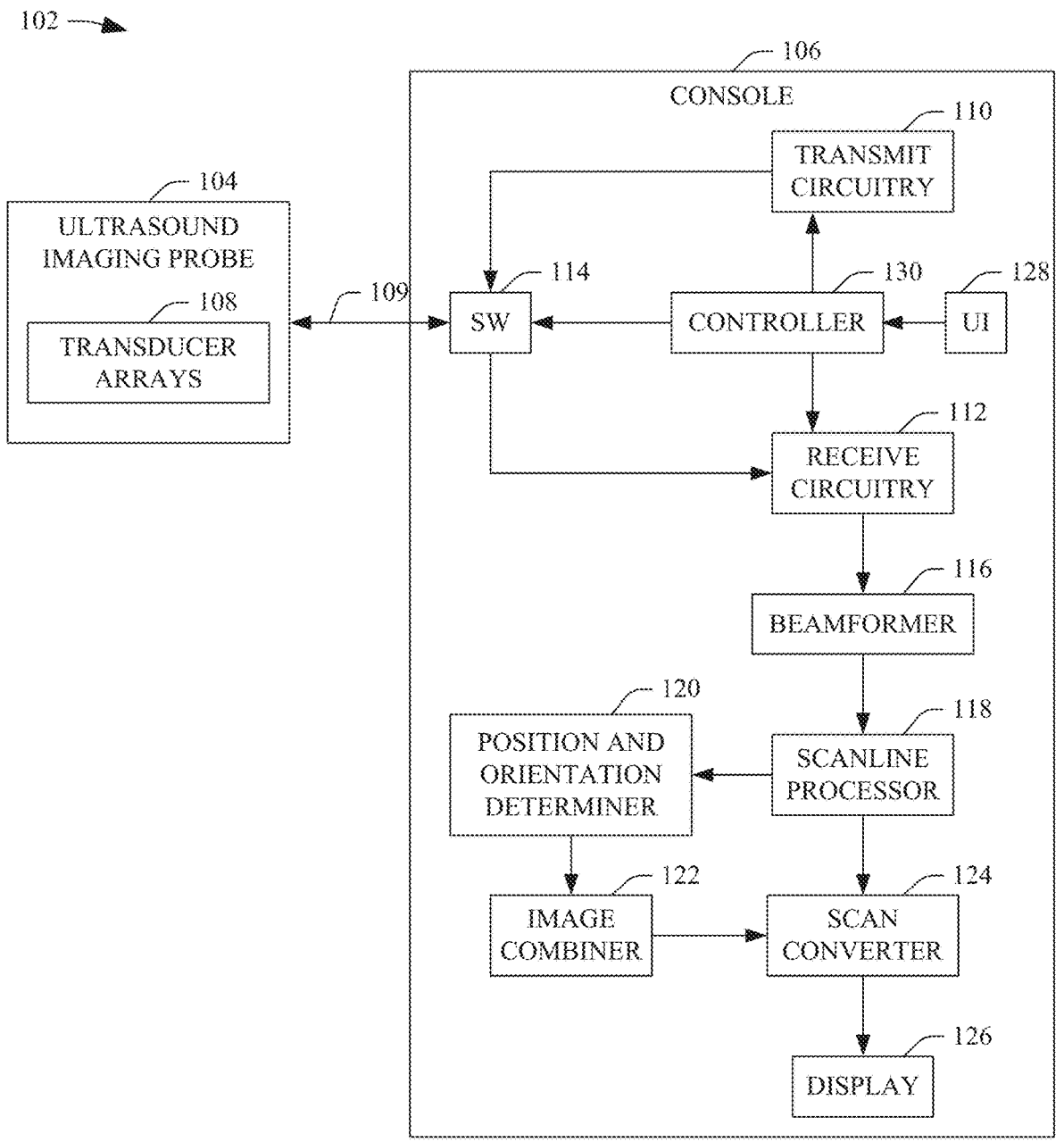
FIG. 1 schematically illustrates an example ultrasound imaging system with an ultrasound imaging probe configured with an articulating shaft and for an ultrasound image-guided neurosurgery procedure through a burr hole in the skull of a patient, in accordance with an aspect of an embodiment(s) herein.

Initially referring to FIG. 1, a non-limiting example of an ultrasound imaging system 102 is schematically illustrated. The ultrasound imaging system 102 includes an ultrasound imaging probe 104 and a console 106.

In the illustrated embodiment, the ultrasound imaging probe 104 and the console 106 interface with each other via a communication channel 109. In one instance, the communication channel 109 includes wired technology, e.g., complimentary interfaces and a cable therebetween. In another instance the communication channel 109 includes wireless technology, e.g., Wi-Fi, etc. In yet another instance the communication channel 109 includes a combination of wired and wireless technology. In yet another instance, the ultrasound imaging probe 104 and the console 106 are integrated in a same housing such as part of a hand-held ultrasound system, etc.

The ultrasound imaging probe 104 includes at least two rigid transducer arrays 108. As described in greater detail below at least in connection with FIGS. 2-9, the at least two rigid transducer arrays 108 are arranged in an elongated flexible shaft along a long axis of the elongated flexible shaft with flexible gaps between the at least two rigid transducer arrays 108 such that each of the at least two rigid transducer arrays 108 can independently articulate relative to each other only in-plane, where each of the at least two rigid transducer arrays 108 is small enough to fit throw a burr hole and an aggregate of the at least two rigid transducer arrays 108 provide an acoustic aperture that is larger than an acoustic aperture of any of the individual at least two rigid transducer arrays 108.

Each of the at least two transducer arrays 108 includes one or more transducer elements. Examples of such arrays include 64, 128, 192, 256, and/or other number of elements, including larger and smaller arrays, one dimensional (1-D) or two dimensional (2-D), etc. Each of the at least two rigid transducer arrays 108 can be linear, curved, and/or otherwise shaped, fully populated, sparse and/or a combination thereof, etc. The one or more transducer elements are configured to convert an excitation electrical signal to an ultrasound pressure field and convert a reflected ultrasound pressure field to an electrical signal.

By way of non-limiting example, the one or more transducer elements can be selectively excited via an excitation electrical (pulsed) signal, which causes at least a sub-set of the transducer elements to transmit an ultrasound pressure field into an examination or scan field of view. The ultrasound pressure field may include a focused ultrasound beam, a defocused (spherical) wave, and/or other ultrasound signal. The one or more transducer elements receive echo signals and generate analog electrical signals indicative thereof. The echo signals are generated in response to the transmitted ultrasound pressure field interacting with structure, such as tissue, blood cells flowing in a portion of a vessel, etc.

The console 106 includes a transmit circuitry 110 configured to generate the excitation electrical signal provided to the at least two rigid transducer arrays 108 for transmitting the ultrasound pressure field. In one instance, this includes generating delays to individual elements of the at least one element of the at least two rigid transducer arrays 108, e.g., for transmit focusing, beam steering, etc.

The console 106 further includes a receive circuitry 112 configured to receive the analog electrical signals from the at least one element and pre-process the analog electrical signals, e.g., amplify, digitize, focus, and/or otherwise process the analog electrical signals. For example, in one instance the receive circuitry 112 includes an amplifier and a corresponding analog to digital converter (ADC) for each element, where each amplifier amplifies a corresponding analog electrical signal from a micro-volt level to a voltage range of the ADC.

The console 106 further includes a switch ("SW") 114 configured to switch between the transmit circuitry 110 and the receive circuitry 112, e.g., by electrically connecting the transmit circuitry 110 to the transducer arrays 108 for a transmit operation and electrically connecting the receive circuitry 112 to the transducer arrays 108 for a receive operation. In an alternative instance, separate switches are employed for each of the transmit circuitry 110 and the receive circuitry 112.

The console 106 further includes a beamformer 116. The beamformer 116 is configured to beamform, e.g., via delay-and-sum (e.g., a matched-filter beamformer, etc.) and/or other beamforming, the signals from the receive circuitry 112 and generate radiofrequency (RF) data. With delay-and-sum beamforming, the digital signal for each element is delayed to align the signals in time, amplified, and then summed. In one instance, a matched filter matched to an expected received echo-pulse shape (bandwidth) operates on the signals.

The console 106 further includes a scanline processor 118. When configured for I/Q demodulation, the scanline processor 118 down mixes the RF signal and optionally applies low pass filtering and/or decimation. This may include employing a Hilbert Transform, a combination of a Complex-Demodulation Band Pass Filter and optional decimation, and/or other processing. The scanline processor 118 detects, extracts and outputs an envelope (i.e., an amplitude) of the I/Q signal (or the RF signal where I/Q modulation is omitted). In one instance, this is achieved using a Hilbert Transform and/or other approach.

The scanline processor 118 compresses the extracted envelope, reducing the dynamic range, e.g., to reduce the dynamic range to a predetermined display precision by a logarithmic (log)-based dynamic range compression and/or otherwise, and outputs a scanline. The scanline processor 118 outputs the processed scanlines as a frame/image (e.g., a B-mode image). The scanline processor 118 may apply other processing such as filtering (e.g., via a Finite Impulse Response (FIR) filter, an Infinite Impulse Response (IIR) filter, etc.), Time Gain Compensation (TGC), noise rejection, and/or other processing.

The console 106 further includes a transducer array position and orientation determiner 120. The position and orientation determiner 120 is configured to determine a relative position and orientation of each of the transducer arrays in the at least two rigid transducer arrays 108 with respect to each other. As described in greater detail below at least in connection with FIGS. 10-12, an overlap between images generated by the individual transducer arrays is known when the elongated flexible shaft 202 is not articulated, and the position and orientation determiner 120 is configured to determine the image overlap, and, based on the image overlap, determine a spatial position and orientation of each of the transducer arrays of the at least two rigid transducer arrays 108.

The console 106 further includes an image combiner 122. The image combiner 122 is configured to combine individual images of the at least two rigid transducer arrays 108 to create a composite image with an acoustic aperture that is larger than an acoustic aperture for an image for any individual array of the multiple transducer arrays 108. As described in greater detail below at least in connection with FIGS. 10-12, this is achieved based on the determined relative position and/or orientation of each of the transducer arrays, along with, e.g., features extracted from the images.

Again, a burr hole for ultrasound image-guided skull-based neurosurgery procedures has been around 4-14 mm in diameter, which limits a size of the tip of the probe to less than 4-14 mm in any direction, i.e., so that the tip of the ultrasound imaging probe and a surgical instrument such as a biopsy needle, etc. can simultaneously fit in the burr hole, which limits the size of the transducer array in azimuth and hence the acoustic aperture of the transducer array, which limits the achievable image quality. The approach described herein overcomes this limitation, providing an improvement in the technology and/or technological field.

The console 106 further includes a scan converter 124 and a display 126. The scan converter 124 is configured to scan convert the individual and/or composite image into a coordinate system of the display 126. The scan converter 124 can be configured to employ analog and/or digital scan converting techniques. The scan converted data can be displayed on the display 126 and/or other display monitor.

The console 106 further includes a user interface ("UI") 128. The user interface 128 includes one or more input devices (such as a button, a knob, a slider, a touch screen, a mouse, a keyboard, etc.) and/or other input device, and/or one or more output devices such as a visible, audible, etc. indicator. The user interface 128 allows a user to control an operation of the system 102. For example, in one instance, the user interface 128 receives an input instructing the display of an individual image(s) and/or the composite image.

The console 106 further includes a controller 130. The controller 130 includes a processor(s) such as a microprocessor (uP), a central processing unit (CPU), a graphics processing unit (GPU), etc., and memory, which stores the adaptive spatial compounding algorithm described herein. The controller 130 is configured to control one or more of the transmit circuitry 110, the receive circuitry 112, the switch 114, the beamformer 116, the scanline processor 118, the transducer array position and orientation determiner 120, the image combiner 122, the scan converter 124, the display 126, and/or the user interface 128. One or more of these components can be implemented in software and/or hardware.

Although the console 106 is described above as separate from the ultrasound imaging probe 104, some or all of the components and/or functions provided by the console 106 can be contained within the ultrasound imaging probe 104. For example, in one instance the ultrasound imaging probe 104 includes transmit circuitry, a switch, receive circuitry, and a first stage of beamforming. In another instance, where the ultrasound imaging probe 104 is configured as a hand-held probe, one or more of the components and/or functions are within a handle of the ultrasound imaging probe 104. Other configurations are also contemplated herein.

Figures 2, 3, 4, 5, 6:
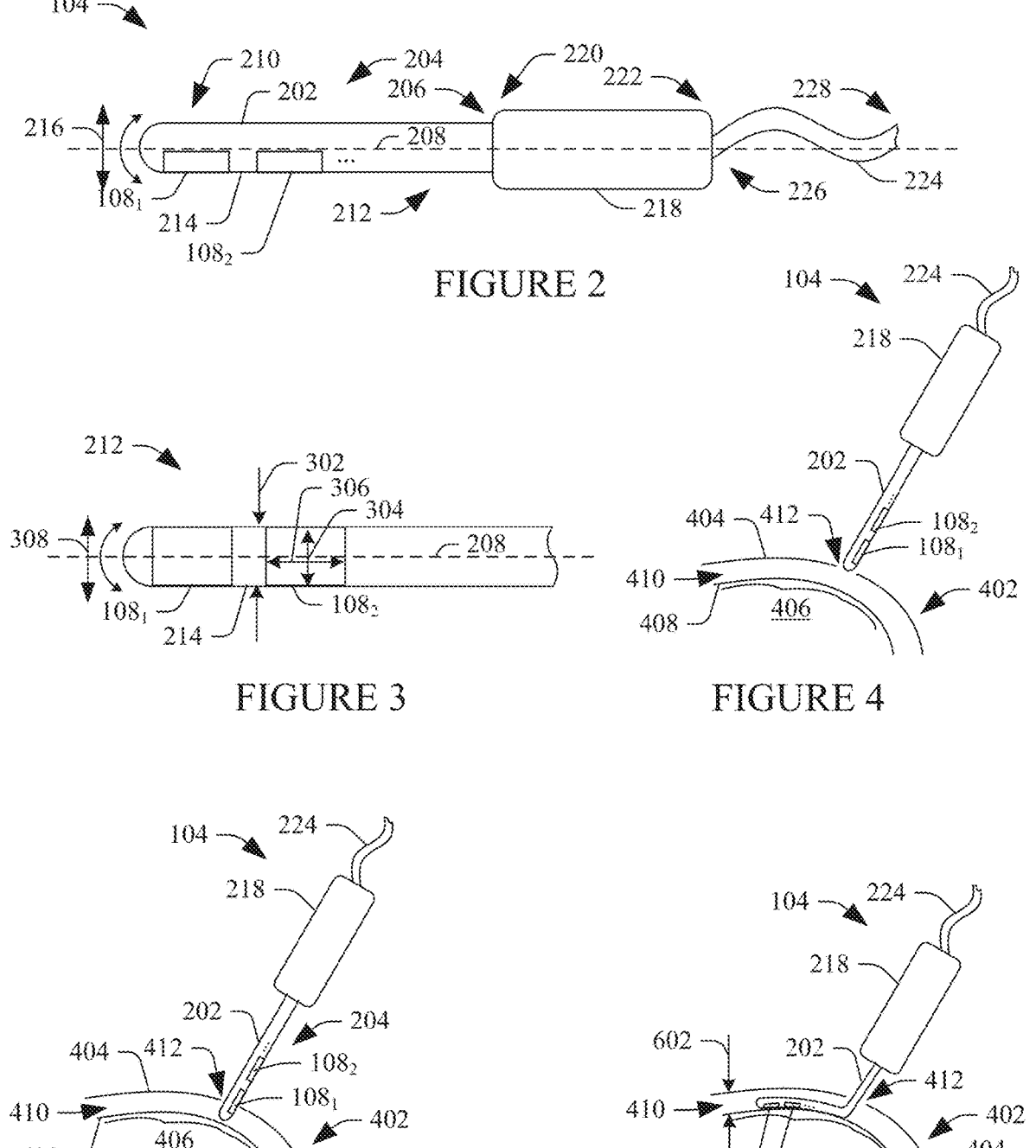
FIG. 2 schematically illustrates a side view of an example of the ultrasound imaging probe discussed in connection with FIG. 1, in accordance with an aspect of an embodiment(s) herein.
FIG. 3 schematically illustrates a bottom view of the example of the ultrasound imaging probe discussed in connection with FIG. 2, in accordance with an aspect of an embodiment(s) herein.
FIG. 4 schematically illustrates the example of the ultrasound imaging probe discussed in connection with FIGS. 2 and 3 outside of a burr hole in a skull of a patient, in accordance with an aspect of an embodiment(s) herein.
FIG. 5 schematically illustrates the example of the ultrasound imaging probe discussed in connection with FIGS. 2 and 3 with a tip at an end of a shaft inside of the burr hole in the skull of the patient, in accordance with an aspect of an embodiment(s) herein.
FIG. 6 schematically illustrates the example of the ultrasound imaging probe discussed in connection with FIGS. 2 and 3 with the shaft articulated in the subdural space between the dura and the brain of the patient, in accordance with an aspect of an embodiment(s) herein.

Turning to FIG. 2, a side view of an example of the ultrasound imaging probe 104 is schematically illustrated. In this example, the ultrasound imaging probe 104 includes an elongated flexible shaft 202 having a first end region 204, a second opposing end region 206, a long axis 208, a top region 210, and a bottom region 212. The elongated flexible shaft 202 includes the at least two transducer arrays, including a first transducer array $108_1$, a second transducer array $108_2$, . . . . The first transducer array $108_1$, the second transducer array $108_2$, . . . are arranged in the bottom region 212 on and along the long axis 208 of the shaft 202, separated from each other via a flexible gap 214 of the elongated flexible shaft 202. As such, in this example, the ultrasound imaging probe 104 is configured as a side-fire probe. For explanatory purposes, the first end region 204 is described as circular in shape, but could be otherwise shaped such as oval, rectangular, square, trapezoidal, etc.

Briefly turning to FIG. 3, a view from the bottom 212 the elongated flexible shaft 202 is schematically illustrated. The elongated flexible shaft 202 has a cross-sectional dimension 302 that is smaller than a diameter of a burr hole. In general, for example, for non-circular shapes, the largest dimension is smaller than a diameter of a burr hole. Each of the at least two rigid transducer arrays 108 (i.e., the first transducer array $108_1$, the second transducer array $108_2$, . . . ) has a width 304 in an elevation direction of the array and a length 306 in an azimuth direction of the array. A size of the width 304 is within a size of the dimension 302. The length 306 is such that an aggregate length of the lengths of the at least two rigid transducer arrays 108 is greater than the diameter of the burr hole, while each the lengths 306 is smaller than a depth of the subdural space, as described in greater detail below.

The elongated flexible shaft 202 is configured to articulate at the flexible gap 214 in a single plane. With reference to FIG. 2, the elongated flexible shaft 202 is configured to articulate at the flexible gap 214 only in-plane, i.e., in a plane 216 that includes the image plane of the ultrasound imaging probe 104. In one instance, articulation is limited as such by connecting the two or more rigid transducer arrays with hinge components, e.g., mechanical hinges, narrow strips of flexible material between the rigid two or more rigid transducer arrays etc. With reference to FIG. 3, the elongated flexible shaft 202 is rigid and does not articulate at the gap 214 in a plane 308, which is orthogonal to the plane 216 (FIG. 2) of the ultrasound imaging probe 104. In one instance, articulation is constrained as such by reinforcing the shaft 202 in such a way that a stiffness is greater in an out-of-plane direction relative to an in-plane direction.

With reference to FIGS. 2 and 3, in one instance, the elongated flexible shaft 202 automatically articulates in the single plane upon engaging a structure. That is, the elongated flexible shaft 202 maintains its normal state of being straight and then upon physically contacting a structure, the elongated flexible shaft 202 begins to bend at the flexible gap 214. Additionally, or alternatively, the elongated flexible shaft 202 is semi-automatically and/or manually articulated by a user via mechanical and/or electro-mechanical subsystem. For example, the U.S. Pat. No. 5,680,863 discusses cables actuated by pulleys or threaded rods. The approach described in U.S. Pat. No. 5,680,863, using cables actuated by pulleys or threaded rods, and/or other approaches are contemplated herein. In general, any known and/or other approach is contemplated herein.

Returning to FIG. 2, the ultrasound imaging probe 104 further includes a handle 218 having a first end region 220 and second end region 222. The second opposing end region 206 of the shaft 202 is coupled to the first end region 220 of the handle 218. The ultrasound imaging probe 104 further includes a cable 224 having a first end region 226 and second end region 228. The second end region 222 of the handle 218 is coupled to the first end region 226 of the cable 224. In the illustrated example, the cable 224 is fixedly coupled to the handle 218. In another instance, the cable 224 is removably coupled to the handle 218, e.g., via complementary connections. The second end region 228 of the cable 224 is coupled to a connector and/or directly to the console 106 (FIG. 1).

FIGS. 4, 5 and 6 graphically illustrate example articulation of the elongated flexible shaft 202 of the ultrasound imaging probe 104. Referring initially to FIG. 4, a head 402 of a patient includes a skull 404, a brain 406, dura 408, and a subdural space 410. A burr hole 412 has been drilled into the skull 404. In FIG. 4, the ultrasound imaging probe 104 is positioned such that the entirety of the elongated flexible shaft 202 is outside of the burr hole 412 ready to be advanced into the burr hole 412. In FIG. 5, the first end region 204 is in the burr hole 412 in the subdural space 410. In FIG. 6, the elongated flexible shaft 202 articulated with a curvature of the brain 406, such that the first transducer array 108$_1$, the second transducer array 108$_2$, . . . are adjacent to and follow a contour of the brain 406. Although this example depicts the first end region 204 in the subdural space 410, more generally, the first end region 204 is navigated in a space under the skull bone, and other locations under the skull are contemplated herein, e.g., the subarachnoid space, etc.

For such articulation, the length 306 (FIG. 3) of each of the rigid two or more transducer arrays 108 (i.e., the first transducer array 108$_1$, the second transducer array 108$_2$, . . . ) is smaller than a depth 602 of the subdural space 410 such an entirety of the each of the rigid two or more transducer arrays 108 can bend at the brain 406 and conform to a shape of a surface of the brain 406 without physically contacting a side of the burr hole 412. The first transducer array 108$_1$, the second transducer array 108$_2$, . . . together provide an acoustic aperture that is greater than the diameter of the burr hole 412. As such, the ultrasound imaging probe 104 described herein mitigates shortcomings of existing probe configured for ultrasound image-guided skull-based neurosurgery procedures, where the transducer aperture is limited to being smaller than the diameter of the burr hole 412. In one instance, this allows for increased image quality relative to other configurations of ultrasound imaging probes.

Figure 7:
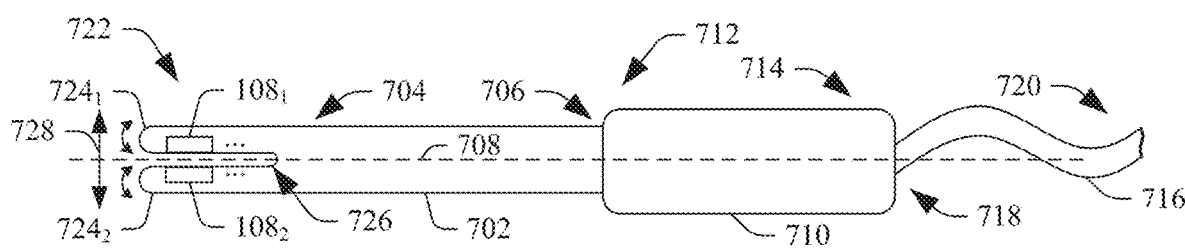
FIG. 7 schematically illustrates a side view of another example of the ultrasound imaging probe discussed in connection with FIG. 1, in accordance with an aspect of an embodiment(s) herein.

Turning now to FIG. 7, a side view of another example of the ultrasound imaging probe 104 is schematically illustrated. The ultrasound imaging probe 104 includes an elongated flexible shaft 702 having a first end region 704, a second opposing end region 706, and a long axis 708. The ultrasound imaging probe 104 further includes a handle 710 having a first end region 712 and second end region 714. The second opposing end region 706 of the elongated flexible shaft 702 is coupled to the first end region 712 of the handle 710. The ultrasound imaging probe 104 further includes a cable 716 having a first end region 718 and second end region 720. The second end region 714 of the handle 710 is coupled to the first end region 718 of the cable 716. The second end region 720 of the cable 716 is coupled to a connector and/or directly to the console 106 (FIG. 1).

In this example, the first end region 704 of the elongated flexible shaft 702 includes a flexible bifurcated tip 722 that includes at least a first branch 724$_1$ and a second branch 724$_2$. The first branch 724$_1$ includes at least one transducer array (e.g., the first transducer array 108$_1$) and the second branch 724$_2$ includes at least one transducer array (e.g., the second transducer array 108$_2$). Similar to the example described in connection with FIGS. 2 and 3, where each branch includes the at least two rigid transducer arrays 108, the at least two rigid transducer arrays 108 of each branch are arranged along the long axis 708 of the elongated flexible shaft 702, separated from each other via a gap of the flexible bifurcated tip 722. In another instance, one or more of the first branch 724$_1$ and the second branch 724$_2$ includes only one of the at least two rigid transducer arrays 108.

In this example, the flexible bifurcated tip 722 extends from a junction 726 of the elongated flexible shaft 702 at which the portion of the elongated flexible shaft 702 between the flexible bifurcated tip 722 and the handle 710 is not configured to flex. Similar to the example described in connection with FIG. 2, the first branch 724$_1$ and the second branch 724$_2$ are configured to articulate at flexible gaps between transducer arrays therein and/or at the junction 726, in a single plane, in-plane. In this example, the first branch 724$_1$ and the second branch 724$_2$ independently articulate. Similar to the example described in connection with FIGS. 2 and 3, articulation can be limited to a single plane through hinge components, stiffeners, and/or the like. In addition, the elongated flexible shaft 702 can be configured to automatically articulate and/or articulate via a user.

Similar to the example described in connection with FIGS. 2 and 3, the flexible bifurcated tip 722 of the elongated flexible shaft 702 (i.e., the combination of the first branch 724$_1$ and the second branch 724$_2$) has a maximum dimension that is smaller than a diameter of the burr hole 412. Each of the at least two transducer arrays 108 of each of the first branch 724$_1$ and the second branch 724$_2$ has a width in an elevation direction of the array and a length in an azimuth direction of the array, where an aggregate of the widths is within the maximum dimension, and an aggregate of the lengths is such that a total length of the at least two transducer arrays 108 is greater than the diameter of the burr hole, while the length of each of the at least two transducer arrays 108 in each of the first branch 724$_1$ and the second branch 724$_2$ is smaller than a size of the subdural space, as described herein.

Figure 8:
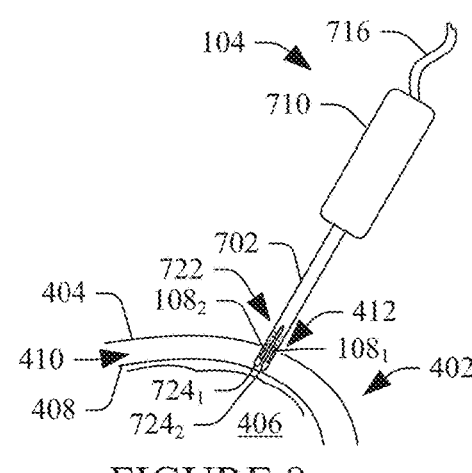
FIG. 8 schematically illustrates the example of the ultrasound imaging probe discussed in connection with FIG. 7 with a tip at an end of a shaft inside a burr hole in a skull of a patient, in accordance with an aspect of an embodiment(s) herein.
Figure 9:
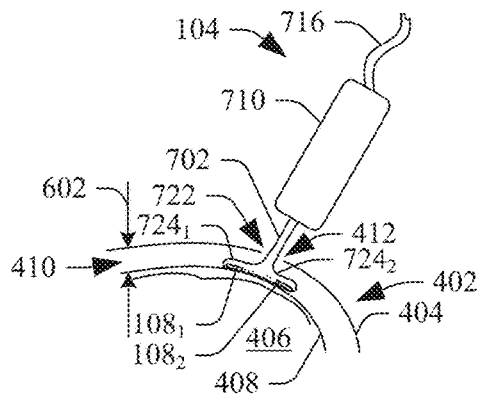
FIG. 9 schematically illustrates the example of the ultrasound imaging probe discussed in connection with FIG. 7 with the shaft articulated in the subdural space between the dura and the brain of the patient, in accordance with an aspect of an embodiment(s) herein.

FIGS. 8 and 9 graphically illustrate example articulation of the first branch 724$_1$ and the second branch 724$_2$ of the flexible bifurcated tip 722 of the elongated flexible shaft 702. Similar to FIGS. 4, 5 and 6, FIGS. 8 and 9 graphically illustrate the head 402 of the patient with the skull 404, the brain 406, the dura 408, and the subdural space 410, along with the burr hole 412 drilled into the skull 404. In FIG. 8, the ultrasound imaging probe 104 is positioned such that a sub-portion (but not all) of the flexible bifurcated tip 722 of the elongated flexible shaft 702 is in the burr hole 412 in the subdural space 410. In FIG. 9, the ultrasound imaging probe 104 is positioned such that the flexible bifurcated tip 722 of the elongated flexible shaft 702 is in the burr hole 412 and has articulated with a curvature of the brain 406, such that the first transducer array 108$_1$, the second transducer array 108$_2$, . . . are adjacent to the brain 406, on opposing sides of the burr hole 412.

Similar to another example described in connection with FIGS. 2-6, for such articulation, the length of each rigid transducer array of the at least two transducer arrays 108 for each of the first branch 724$_1$ and the second branch 724$_2$ is smaller than the depth 602 of the subdural space 410 such an entirety of the each rigid transducer array of the multiple transducer arrays 108 for each of the first branch 724$_1$ and the second branch 724$_2$ can independently bend at the dura 408 and conform to a shape of a surface of the dura 408 without physically contacting a side of the burr hole 412. By flexing the bifurcated tip 722 at the junction 726, this configuration allows for producing an image centered directly under the burr hole, while still constraining articulation to one dimension.

Similar to another example described in connection with FIGS. 2-6, the first transducer array 108$_1$ and the second transducer array 108$_2$ together provide an acoustic aperture that is greater than the diameter of the burr hole 412, while together the flexible bifurcated tip 722 is no larger than the diameter of the burr hole 412. As such, the ultrasound imaging probe 104 described herein mitigates shortcomings of existing probes configured for ultrasound image-guided skull-based neurosurgery procedures, where the transducer aperture is limited to being smaller than the diameter of the burr hole 412. Again, this allows for increased image quality relative to other configurations of ultrasound imaging probes.

Figure 10:
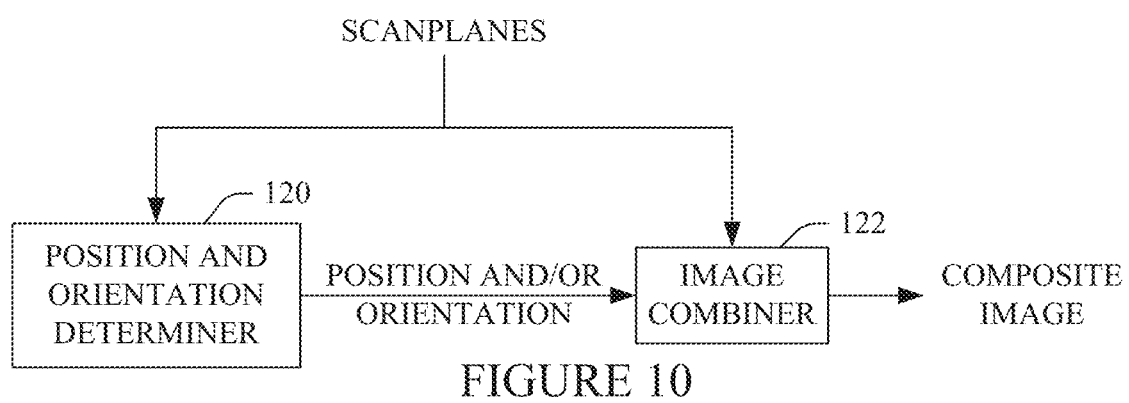
FIG. 10 schematically illustrates an example of the transducer array position and orientation determiner and the image combiner of the console, in accordance with an aspect of an embodiment(s) herein.
Figure 11:
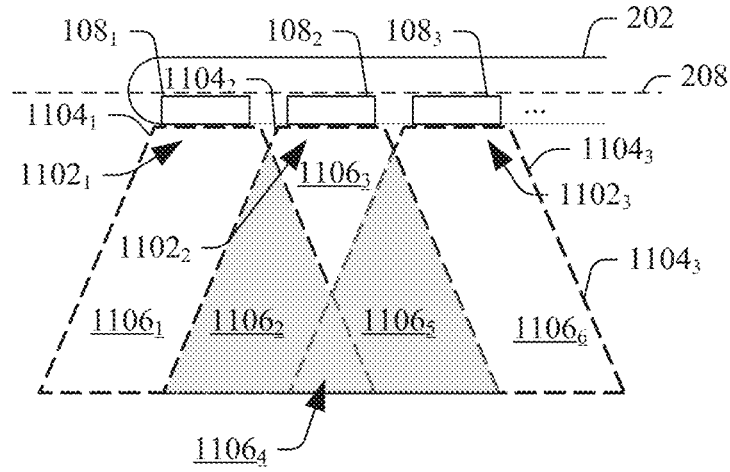
FIG. 11 schematically illustrates an example of image planes of transducer arrays of the ultrasound imaging probe with the shaft in a non-articulated state, in accordance with an aspect of an embodiment(s) herein.
Figure 12:
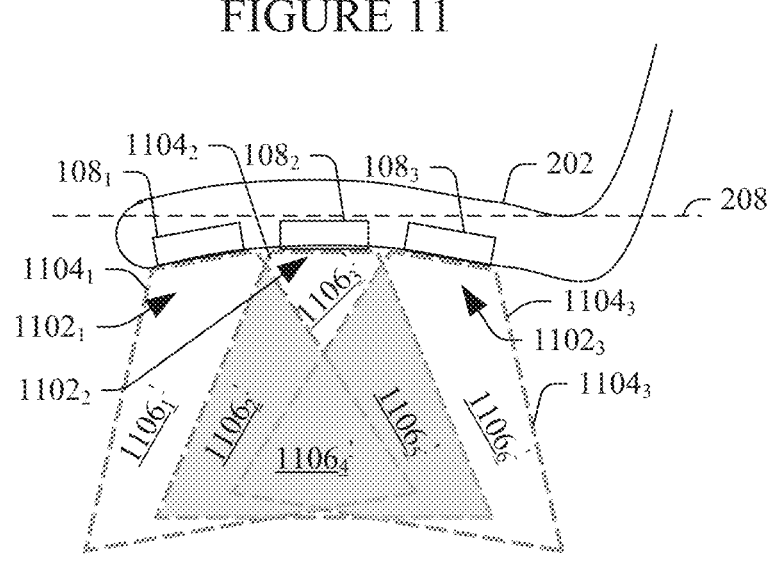
FIG. 12 schematically illustrates an example of image planes of transducer arrays of the ultrasound imaging probe with the shaft in an example articulated state, in accordance with an aspect of an embodiment(s) herein.

Moving to FIG. 10, an example of the position and orientation determiner 120 and the image combiner 122 is schematically illustrated. The position and orientation determiner 120 receives, as input, scanlines from the scanline processor 118 (FIG. 1). In one instance, the position and orientation determiner 120 is configured to determine the position and orientation based on overlapping regions of the images of the individual arrays of the two or more rigid transducer arrays 108. FIGS. 11 and 12 illustrate overlapping regions for a non-articulated elongated flexible shaft 202 (FIG. 11) and overlapping regions for an articulated elongated flexible shaft 202 (FIG. 12).

Initially referring to FIG. 11, the elongated flexible shaft 202 is in a non-articulated state in which the two or more rigid transducer arrays 108 are all aligned in a straight line along the long axis 208 of the elongated flexible shaft 202. The elongated flexible shaft 202 includes the first transducer array $108_1$, the second transducer array $108_2$, a third transducer array 1083, . . . . Each of the first transducer array $108_1$, the second transducer array $108_2$, a third transducer array $108_3$, . . . has a respective acoustic aperture, including a first acoustic aperture $1102_1$, a second acoustic aperture $1102_2$, a third acoustic aperture $1102_3$, . . . . Each of the first acoustic aperture $1102_1$, the second acoustic aperture $1102_2$, the third acoustic aperture $1102_3$, . . . has a corresponding image plane, including a first image plane $1104_1$, a second image plane $1104_2$, a third image plane $1104_3$.

A first region $1106_1$ represents a first sub-portion (i.e., less than all) of the first image plane $1104_1$ with no overlap. A second region $1106_2$ represents a second sub-portion of the first image plane $1104_1$ and a first sub-portion of the second image plane $1104_2$ that overlap. A third region $1106_3$ represents a second sub-portion of the second image plane $1104_2$ with no overlap. A fourth region $1106_4$ represents a third sub-portion of the first image plane $1104_1$, a third sub-portion of the second image plane $1104_2$ and a first sub-portion of the third image plane $1104_3$ that overlap. A fifth region $1106_5$ represents a fourth sub-portion of the second image plane $1104_2$ and a second sub-portion of the third image plane $1104_3$ that overlap. A sixth region $1106_6$ represents a third first sub-portion of the third image plane $1104_3$ with no overlap.

The spatial relationship of the first image plane $1104_1$, the second image plane $1104_2$, the third image plane $1104_3$, . . . , along with their non-overlapping regions and overlapping regions, is known for a non-articulated elongated flexible shaft 202. For example, in one instance a center-to-center spacing of the two or more transducer arrays 108 for the ultrasound imaging probe 104 is known for when the elongated flexible shaft 202 is not articulated and hence an overlap of the images generated thereby is known for when the elongated flexible shaft 202 is not articulated. The position and orientation determiner 120 is configured to determine the image overlap, and, based on the image overlap determines a spatial position and orientation of each of the transducer arrays of the two or more transducer arrays 108.

Turning to FIG. 12, the elongated flexible shaft 202 is in an articulated state in which the two or more rigid transducer arrays 108 are no longer aligned in a straight line along the long axis 208 of the elongated flexible shaft 202. The elongated flexible shaft 202 includes the first transducer array $108_1$, the second transducer array $108_2$, the third transducer array $108_3$, . . . , the first acoustic aperture $1102_1$, the second acoustic aperture $1102_2$, the third acoustic aperture $1102_3$, and the first image plane $1104_1$, the second image plane $1104_2$, the third image plane $1104_3$, In this example, a first region $1106_1$ represents a first sub-portion (i.e., less than all) of the first image plane $1104_1$ with no overlap. A second region $1106_2$ represents a second sub-portion of the first image plane $1104_1$ and a first sub-portion of the second image plane $1104_2$ that overlap. A third region $1106_3$ represents a second sub-portion of the second image plane $1104_2$ with no overlap. A fourth region $1106_4$ represents a third sub-portion of the first image plane $1104_1$, a third sub-portion of the second image plane $1104_2$ and a first sub-portion of the third image plane $1104_3$ that overlap. A fifth region $1106_5$ represents a fourth sub-portion of the second image plane $1104_2$ and a second sub-portion of the third image plane $1104_3$ that overlap. A sixth region $1106_6$ represents a third first sub-portion of the third image plane $1104_3$ with no overlap.

Wither reference to FIGS. 11 and 12, a change in the first region $1106_1$, the second region $1106_2$, the third region $1106_3$, the fourth region $1106_4$, the fifth region $1106_5$, and the sixth region $1106_6$ to the first region $1106_1$, the second region $1106_2$, the third region $1106_3$, the fourth region $1106_4$, the fifth region $1106_5$, and the sixth region $1106_6$ is due to the articulation in the elongated flexible shaft 202 and corresponds to the changing spatial position of the first transducer array $108_1$, the second transducer array $108_2$, the third transducer array $108_3$, . . . two or more rigid transducer arrays. The position and orientation determiner 120 determines the change in the overlap, and based thereon, determines the position and orientation of each of the first transducer array $108_1$, the second transducer array $108_2$, the third transducer array $108_3$, The image combiner 122 receives, as input, the scanlines from the scanline processor 118 (FIG. 1) and the position and orientation of each of the first transducer array $108_1$, the second transducer array $108_2$, the third transducer array $108_3$, . . . from the position and orientation determiner 120 and combines at least two of the first image plane $1104_1$, the second image plane $1104_2$, the third image plane $1104_3$, . . . to create an image plane that is wider in azimuth than any of the individual image planes, i.e., the first image plane $1104_1$, the second image plane $1104_2$, the third image plane $1104_3$, In one instance, the image combiner 122 registers the first image plane $1104_1$, the second image plane $1104_2$, the third image plane $1104_3$, . . . based on features in the first image plane $1104_1$, the second image plane $1104_2$, the third image plane $1104_3$, . . . . In one instance, this includes extracting certain features from the first image plane $1104_1$, the second image plane $1104_2$, the third image plane $1104_3$, . . . and then registering the first image plane $1104_1$, the second image plane $1104_2$, the third image plane $1104_3$, . . . based on the extracted features. An example approach is described in US patent application, 2022/0087638 A1, entitled "Image Fusion-Based Tracking without a Tracking Sensor," and filed Sep. 18, 2020, the entirety of which is incorporated herein by reference.

Figure 13:
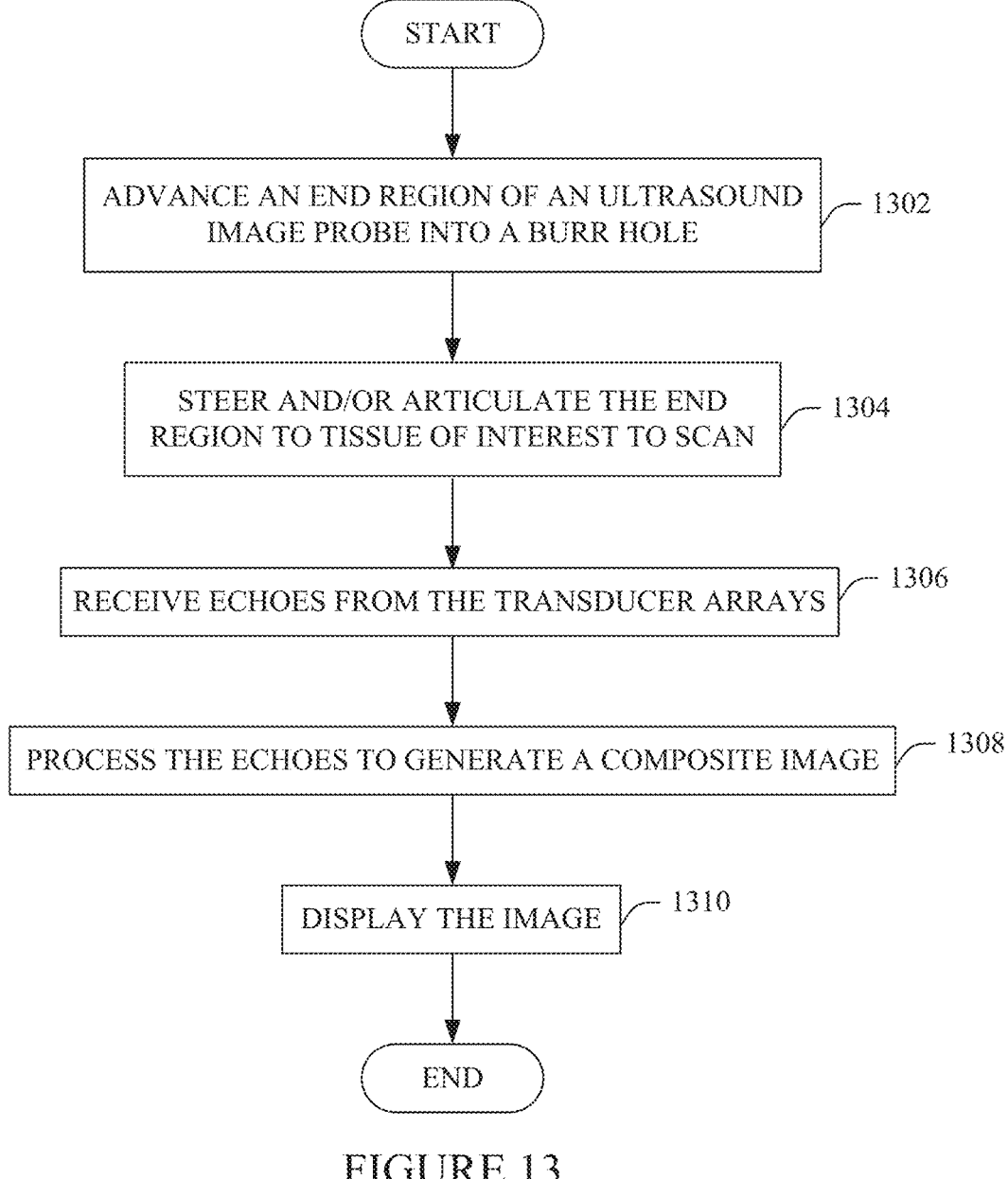
FIG. 13 illustrates a non-limiting example of a flow chart for a computer-implemented method for employing an ultrasound imaging probe with a non-bifurcated tip for an ultrasound image-guided neurosurgery procedure through a burr hole in the skull of a patient, in accordance with an aspect of an embodiment(s) herein.

FIG. 13 illustrates a non-limiting example of a flow chart for a computer-implemented method for an image-guided neurosurgery procedure through a burr hole in a skull of a patient with a side-fire ultrasound imaging probe having a non-bifurcated tip. It is to be appreciated that the ordering of the acts in the method is not limiting. As such, other orderings are contemplated herein. In addition, one or more acts may be omitted, and/or one or more additional acts may be included.

At 1302, a tip of side-fire ultrasound imaging probe configured for an image-guided neurosurgery procedure through a burr hole in a skull of a patient is advanced through the burr hole, as described herein and/or otherwise. The side-fire ultrasound imaging probe includes an elongated shaft with a long axis, the at least the first rigid transducer array and the second rigid transducer array arranged along the long axis, and an articulating region between the at least the first rigid transducer array and the second rigid transducer array, the at least the first rigid transducer array and the second rigid transducer array are arranged in a straight line on the long axis of the elongated shaft, and a largest cross-sectional dimension of the first end region is smaller than a diameter of the burr hole in the skull of the patient.

At 1304, the elongated shaft is steered and articulated only in an in-plane direction in a cavity of the skull to position the at least the first rigid transducer array and the second rigid transducer array to image tissue of interest, as described herein and/or otherwise. At 1306, echoes are received by at least the first rigid transducer array and the second rigid transducer array, as described herein and/or otherwise. At 1308, the echoes are processed to generate a composite image with an acoustic aperture that is larger than an acoustic aperture of images generated for individual arrays of the at least the first rigid transducer array and the second rigid transducer array, as described herein and/or otherwise.

At 1310, the composite image is displayed, as described herein and/or otherwise. In one instance, the processing includes generating an individual image for each of the at least the first rigid transducer array and the second rigid transducer array, determining a position and orientation of each of the at least the first rigid transducer array and the second rigid transducer array based on overlapping regions of the individual images, and combining the individual images to generate the composite image based on the determined position and orientation and on features extracted from the individual images.

Figure 14:
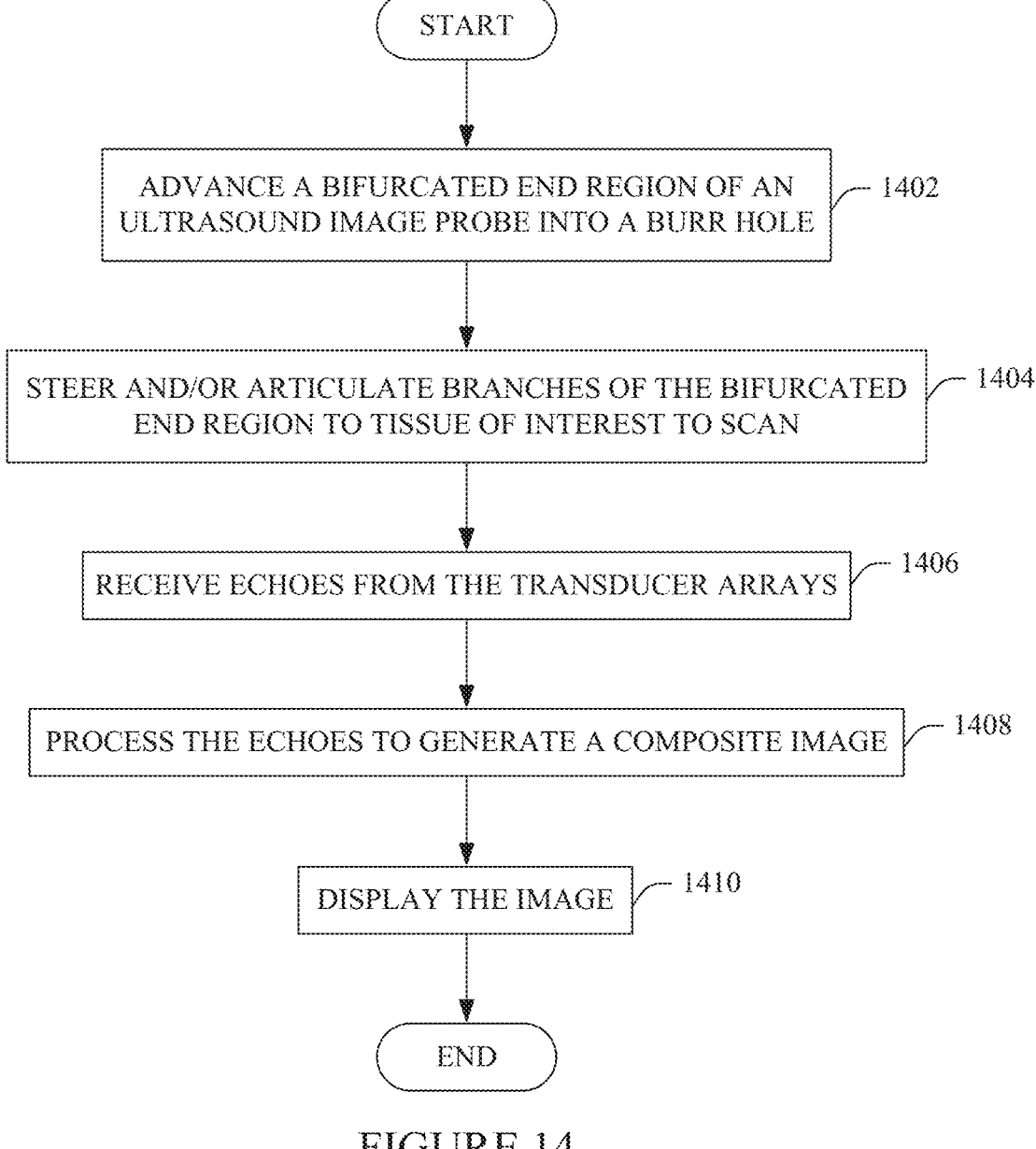
FIG. 14 illustrates a non-limiting example of a flow chart for a computer-implemented method for employing another ultrasound imaging probe with a bifurcated tip for an ultrasound image-guided neurosurgery procedure through a burr hole in the skull of a patient, in accordance with an embodiment(s) herein.

FIG. 14 illustrates a non-limiting example of a flow chart for a computer-implemented method for an image-guided neurosurgery procedure through a burr hole in a skull of a patient with a side-fire ultrasound imaging probe having a bifurcated tip. It is to be appreciated that the ordering of the acts in the method is not limiting. As such, other orderings are contemplated herein. In addition, one or more acts may be omitted, and/or one or more additional acts may be included.

At 1402, a tip of side-fire ultrasound imaging probe configured for an image-guided neurosurgery procedure through a burr hole in a skull of a patient is advanced through the burr hole, as described herein and/or otherwise. The side-fire ultrasound imaging probe includes an elongated shaft with a long axis, the at least the first rigid transducer array and the second rigid transducer array arranged along the long axis, and an articulating region between the at least the first rigid transducer array and the second rigid transducer array, the first end region includes a bifurcated tip with two branches that are parallel to each other along the long axis of the elongated shaft, and each of the two branches includes at least one of the at least the first rigid transducer array and the second rigid transducer array, and a largest cross-sectional dimension of the first end region is smaller than a diameter of the burr hole in the skull of the patient, e.g., smaller than 14 mm.

At 1404, the elongated shaft is steered and articulated only in an in-plane direction in a cavity of the skull to position the at least the first rigid transducer array and the second rigid transducer array to image tissue of interest, as described herein and/or otherwise. At 1406, echoes are received by at least the first rigid transducer array and the second rigid transducer array, as described herein and/or otherwise. At 1408, the echoes are processed to generate a composite image with an acoustic aperture that is larger than an acoustic aperture of images generated for individual arrays of the at least the first rigid transducer array and the second rigid transducer array, as described herein and/or otherwise.

At 1410, the composite image is displayed, as described herein and/or otherwise. In one instance, the processing includes generating an individual image for each of the at least the first rigid transducer array and the second rigid transducer array, determining a position and orientation of each of the at least the first rigid transducer array and the second rigid transducer array based on overlapping regions of the individual images, and combining the individual images to generate the composite image based on the determined position and orientation and on features extracted from the individual images.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only and are thus not intended to limit in any way the definition and/or meaning of the term "computer." The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in jurisdictions that require them, but this should not be taken to mean that the features in the dependent claims are mutually exclusive.

What is claimed is:

1. A side-fire ultrasound imaging probe configured for an image-guided neurosurgery procedure through a burr hole in a skull of a patient, comprising:
  an elongated shaft, including:
    a first end region;
    a second opposing end region;
    a long axis;
    at least a first rigid transducer array and a second rigid transducer array arranged in the first end region along the long axis of the elongated shaft; and
    an articulating region between the at least the first rigid transducer array and the second rigid transducer array; and
  a handle including;
    a first end region, wherein the first end region of the handle is coupled to the second opposing end region of the elongated shaft,
  wherein a largest cross-sectional dimension of the first end region of the elongated shaft is smaller than a diameter of the burr hole in the skull of the patient
  wherein echoes received by the at least the first rigid transducer array and the second rigid transducer array are processed to generate an individual image for each of the at least the first rigid transducer array and the second rigid transducer array,
  wherein a position and orientation of each of the at least the first rigid transducer array and the second rigid transducer array is determined based on overlapping regions of the individual images,
  wherein the echoes received by the at least the first rigid transducer array and the second rigid transducer array are processed based on the determined position and orientation of each of the at least the first rigid transducer array and the second rigid transducer array to generate a composite image with an acoustic aperture that is larger than an acoustic aperture of images generated for individual arrays of the at least the first rigid transducer array and the second rigid transducer array, and
  wherein the composite image is displayed on a display monitor.

2. The side-fire ultrasound imaging probe of claim 1, wherein the burr hole diameter is in a range of four (4) to fourteen (14) millimeters (mm).

3. The side-fire ultrasound imaging probe of claim 1, wherein the at least the first rigid transducer array and the second rigid transducer array respectively have at least a first length in an azimuth direction and a second length in the azimuth direction, and an aggregate length of the at least the first length and the second length is larger than the diameter of the burr hole.

4. The side-fire ultrasound imaging probe of claim 1, wherein the at least the first rigid transducer array and the second rigid transducer array are arranged in a straight line on the long axis of the elongated shaft.

5. The side-fire ultrasound imaging probe of claim 1, wherein the first end region of the elongated shaft includes a bifurcated tip with two branches that are parallel to each other along the long axis of the elongated shaft, and each of the two branches includes at least one of the at least the first rigid transducer array and the second rigid transducer array.

6. The side-fire ultrasound imaging probe of claim 1, wherein the elongated shaft is configured to articulate only in-plane.

7. The side-fire ultrasound imaging probe of claim 1, wherein the elongated shaft is configured to automatically articulate in response to the first end region of the elongated shaft physically contacting structure.

8. The side-fire ultrasound imaging probe of claim 1, wherein the elongated shaft is configured for manual articulation.

9. A method for an image-guided neurosurgery procedure through a burr hole in a skull of a patient, comprising:

receiving echoes by at least a first rigid transducer array and a second rigid transducer array of a side-fire ultrasound imaging probe, wherein the side-fire ultrasound imaging probe includes an elongated shaft with a long axis, the at least the first rigid transducer array and the second rigid transducer array arranged along the long axis, and an articulating region between the at least the first rigid transducer array and the second rigid transducer array, wherein a largest cross-sectional dimension of the first end region is smaller than a diameter of the burr hole in the skull of the patient;

processing the echoes received by the at least the first rigid transducer array and the second rigid transducer array to generate an individual image for each of the at least the first rigid transducer array and the second rigid transducer array;

determining a position and orientation of each of the at least the first rigid transducer array and the second rigid transducer array based on overlapping regions of the individual images;

processing the echoes received by the at least the first rigid transducer array and the second rigid transducer array based on the determined position and orientation of each of the at least the first rigid transducer array and the second rigid transducer array to generate a composite image with an acoustic aperture that is larger than an acoustic aperture of images generated for individual arrays of the at least the first rigid transducer array and the second rigid transducer array; and displaying the composite image on a display monitor.

10. The method of claim 9, further comprising:

articulating the elongated shaft only in-plane.

11. The method of claim 9, further comprising:

steering the elongated shaft in a cavity in the skull.

12. The method of claim 9, further comprising:

combining the individual images to generate the composite image based on features extracted from the individual images.

13. The ultrasound imaging system of claim 9, wherein the burr hole diameter is in a range of 4 to 14 mm.

14. A computer readable medium encoded with computer executable instructions, which, when executed by a processor, cause the processor to:

receive echoes by at least a first rigid transducer array and a second rigid transducer array of a side-fire ultrasound imaging probe during an image-guided neurosurgery procedure through a burr hole in a skull of a patient, wherein the side-fire ultrasound imaging probe includes an elongated shaft with a long axis, the at least the first rigid transducer array and the second rigid transducer array arranged along the long axis, and an articulating region between the at least the first rigid transducer array and the second rigid transducer array, wherein a largest cross-sectional dimension of the first end region is smaller than a diameter of the burr hole in the skull of the patient;

process the echoes received by the at least the first rigid transducer array and the second rigid transducer array to generate an individual image for each of the at least the first rigid transducer array and the second rigid transducer array;

determine a position and orientation of each of the at least the first rigid transducer array and the second rigid transducer array based on overlapping regions of the individual images;

process the echoes received by the at least the first rigid transducer array and the second rigid transducer array based on the determined position and orientation of each of the at least the first rigid transducer array and the second rigid transducer array to generate a composite image with an acoustic aperture that is larger than an acoustic aperture of images generated for individual arrays of the at least the first rigid transducer array and the second rigid transducer array; and display the composite image on a display monitor.

15. The computer readable medium of claim 14, wherein the instructions further cause the processor to:

combine the individual images to generate the composite image based on features extracted from the individual images.

16. The computer readable medium of claim 14, wherein the burr hole diameter is in a range of 4 to 14 mm.

* * * * *